United States Patent [19]

Leach et al.

[11] 4,024,768

[45] May 24, 1977

[54] DETERMINATION OF PARTICLE SIZES

[76] Inventors: Marcel Francis Leach, 1800 Latimer Crescent, Sudbury, Ontario; Gottfried Adolf Rubin, 3269 Parkdale Crescent, Val Caron, Ontario, both of Canada

[22] Filed: Aug. 2, 1976

[21] Appl. No.: 710,409

[30] Foreign Application Priority Data

Aug. 15, 1975 Canada ............................... 234092

[52] U.S. Cl. ................................. 73/432 PS; 73/67
[51] Int. Cl.² .................. G01N 15/02; G01N 29/00
[58] Field of Search .......................... 73/432 PS, 67

[56] References Cited

UNITED STATES PATENTS

| 3,802,271 | 4/1974 | Bertelson ...................... 73/432 PS |
| 3,805,591 | 4/1974 | Willis et al. ................ 73/432 PS X |
| 3,842,656 | 10/1974 | DiBattista .................. 73/432 PS X |

FOREIGN PATENTS OR APPLICATIONS 168,951   2/1965   U.S.S.R. ............................... 73/67

Primary Examiner—Richard C. Queisser
Assistant Examiner—Joseph W. Roskos
Attorney, Agent, or Firm—Robert G. Hirons

[57] ABSTRACT

The average particle diameter and particle size distribution of hard particles in a bed are determined by causing impingement of the particles, e.g. by tumbling them, and recording and analyzing the beat pattern of the sound emanating from the particles as a result of such impingement.

13 Claims, 4 Drawing Figures

SPHERE DIAMETER VS AVERAGE DURATION OF STEEP TROUGH WITHIN A DECAY PATTERN ($\bar{T}$) OR A BEAT ($\bar{\varepsilon}$)

AVERAGE DURATION OF BEAT ENVELOPE ($\bar{\varepsilon}$) VS SPHERE DIAMETER (D)

DETERMINATION OF PARTICLE SIZES

FIELD OF THE INVENTION

This invention relates to processes and apparatus for determining sizes and size distributions of particles of a hard particulate solid material.

BACKGROUND OF THE INVENTION

Methods currently used for particle size determination include counting methods, both optical and electrical, sedimentation methods, separation methods and surface measurement methods. Whilst such methods can be used to make reasonably accurate determinations of particle sizes, they are not generally suitable for use alongside industrial processes. They are either time consuming and tedious to perform, or depend upon the use of complicated and sophisticated apparatus and techniques. They also depend to a large degree upon inherent characteristics of the materials under test, such as density, so that they are of limited use with non-homogeneous particulate mixtures.

BRIEF SUMMARY OF THE INVENTION

The present invention is based upon the discovery that the sound emanating from the collision of hard particles has characteristics depending upon the size of the colliding particles. Thus, by causing the particles of a hard particulate substance to impinge upon one another, e.g. by tumbling the particulate substance, and recording and analyzing the sound produced, the average sizes of the impinging particles, and their particle size distribution, can be determined.

Thus, according to the present invention, there is provided a process of determining average particle sizes and particle size distributions of a plurality of particles of a hard substance, which comprises the steps of:

impinging the particles against one another;

detecting at least a portion of the sound caused by such impingement;

converting the sound into corresponding electrical impulses, and recording the electrical impulses;

analyzing the beat pattern of recorded electrical impulses to determine particle size characteristics of the impinging particles generating said impulses.

Also according to the present invention, there is provided an apparatus for determining average particle sizes and particle size distribution of a hard particulate substance, which comprises in combination:

means for causing impingement of the particles against one another;

sound detecting means in proximity to the location of impingement of the particles against one another and adapted to detect at least a portion the sound of said impingement and convert it to electrical impulses;

at least one amplifier electrically connected to the sound detecting means and adapted to amplify said electrical impulses;

converting means electrically connected to said at least one amplifier to convert the amplified electrical impulses to visual beat patterns or to digital information concerning said beat patterns for subsequent analysis.

According to a preferred aspect of the process of the invention, impingement of the particles is caused by tumbling them in a rotating vessel such as a drum. The sound which is detected, converted and analyzed is over the range 0–200 kilohertz (KHz), preferably over the high frequency range which is inaudible to the human ear, i.e. the range 20–200 KHz. This enables the process to be conducted in the presence of extraneous audible sounds, i.e. in a noisy room or other environment, e.g. alongside machinery or processing equipment since the sound to be analyzed from the particle impingement is generally in the high frequency range.

The sound detecting means is preferably a microphone, which can be pre-set to detect the required frequencies. A specific useful microphone is a miniature 1/8 inch condenser microphone such as Bruel and Kjaer type 4138.

The sound emanating from the impinging particles is amplified and converted by suitable means such as a fast signal analyzer to obtain a beat pattern of varying intensity, or amplitude, of the sound over a very short period of time, of the order of 50–1000 microseconds. Preferably the sound pattern of a single beat or small number (1–5) beats of the emanating sound is recorded. It has been found that the pattern so obtained is composed of the constant harmonics and basic vibrating frequencies of the impinging particles from which the sound emanates. The beat pattern can be analyzed to obtain the necessary information to allow calculation of the average size of the impinging particles, and to allow calculation of other information about the particle sizes such as the particle size distribution.

In one process according to the invention, the fast signal analyzer or fast oscilloscope is arranged to display the beat pattern of the sound on a cathode ray tube screen, or is coupled to a chart recorder so as to obtain a visual display of beat pattern on paper. The beat pattern formed is in effect a graph of sound intensity or amplitude, as vertical axis, against time, as horizontal axis, and has an irregular wave-form appearance. The pattern is a record of the variation of the amplitude of the sound emanating from the colliding particles, over the very short period of time during which the sound was recorded and analyzed by the fast signal analyzer, i.e. the beat period or periods, and over the whole range of frequencies over which the sound was detected. Both the frequency range and the time interval of recording can be present. If now another pattern is recorded at a different time but for the same duration, and over the same frequency range, the second pattern will be another beat pattern and superficially different in appearance but will nevertheless contain characteristics common with the first pattern. These common characteristics are dependent upon the size of the impinging particles from which the size emanates, and can be analyzed to obtain particle size information.

The beat pattern obtained in this manner over a whole range of frequencies such as 0–200 KHz, in effect is the sum of the amplitudes of all the sounds emanating from the impinging particles, over the whole of this frequency range. When the frequency range is set this broadly, the sound emanating from collision of particles of practically all sizes in the mass under investigation is detected, and contributes to the pattern produced. This pattern is, however, dominated by the sounds produced by the particles of average size, and so by analysis of this pattern, information about average particle size can be determined. The pattern itself does not give information about the frequencies of the sounds contributing to the pattern, except that they are all within the present range.

However, the collision of two particles together emits sounds, in the inaudible frequency range, the frequency of which, or the range of frequencies of which, is dependent upon the sizes of the particles in collision. In the process of the invention, therefore, useful information concerning particle size distributions in a bed of particles can be obtained by recording and analyzing the beat patterns produced over various limited frequency ranges. This involves determinations of the intensities of sound produced at the various limited frequency ranges.

Instead of displaying the beat patterns so produced on the screen or on a chart, the fast signal analyzer can if desired by arranged to convert information about the sound emanating from the particle collisions into digital form, for feeding to data processing equipment. By suitably computer processing the data generated, information about average particle size diameters of the impinging particle sizes can be obtained. A pattern generated over a wide frequency range (e.g. 0-200 KHz) can also be analyzed by Fourier analysis, e.g. using a computer, to determine the intensities of the sound at various frequencies which are contributing to this pattern. Thus information on particle size distribution can be determined.

The process of the invention can be conducted with particles of sizes from about 0.1 micron to at least 5 centimeters in average diameter, preferably from 1 micron to 5 centimeters. Particles with diameter of from about 44 microns to about 3 centimeters work particularly well. Particles to be tested can be widely differing sizes within this general range, and do not have to be of uniform size or shape. Nor do they all have to be of the same material.

For the measurement of small size particles by the method of the invention, e.g. particles in the size range 0.1–10 microns, it is preferred to use a tunable ultrasound generator in combination with the impinging particles. Particles of such small sizes will, on impingement, emit sounds which are of too high a frequency for detection by the microphone and subsequent recording and analysis. Accordingly, in this embodiment of the invention, a tunable ultrasound generator is included in proximity to the impinging particles. If a small size particle bed gives no sound signal detectable by the microphone, due to the high frequency thereof, the ultrasound generator is used, and the frequency of its ultrasound emissions varied until those of the impinging particles. Then a beat is generated, of frequency corresponding to the difference in frequency of the ultrasound emissions and the particle impingement emissions. This frequency is readily detectable by the microphone. The beat has a pattern which can be analyzed and recorded, to determine particle sizes according to the process of the invention. This beat sound detection is effectively an indirect detection of the particle impingement sound, since it is derived therefrom.

The types of materials to which the method of invention can be applied are generally hard, particulate materials. The particles should be capable of substantially elastic impact together. They should be impinged in a manner to cause such substantially elastic impact, and to avoid any substantial amount of particle fracture on impact.

In general, the method is applicable to particulate beds of materials such as iron, steel, glass aluminum, copper, hard metals in general, ceramic materials, stone, crushed and particulate minerals such as hard ores and rocks, gravel, sand, coal, crystalline materials such as sugar, salts, etc. It is not generally suited to soft or sticky particulate materials. Thus it is not suitable for use with lead, powdered food-stuffs such as milk powders or flour, or powdered organic drugs.

The best materials for use in the method of the invention are the hard elastic substances such as glass, steel, aluminum, rock, and the like. The method is particularly suited for use with materials having a ratio of Youngs modulus to density $(Y/p)$ in the approximate range of $2 \times 10^7$ meter$^2$/sec$^2$ to $3 \times 10^7$ meter$^2$/sec$^2$.

The apparatus of the present invention preferably includes a drum rotating about an inclined axis, to cause impingement of particles contained therein. If desired, the interior of the drum can be lined with soft cushioning material so that no significant sound is generated by the collision of the particles under test with the walls of the drum. This however is not necessary, since such sounds can be readily identified as to frequency, and filtered out. A A microphone with pre-set frequency range is preferably mounted near the particle bed, to detect the sounds from the impinging particles and convert them to electrical impulses. The microphone is preferably connected to a pre-amplifier, which in turn is connected to an amplifier, which feeds the fast signal analyzer.

A specific fast signal analyzer which can be used is that sold as Model 610 by Biomation Inc. A specific pre-amplifier microphone, is the Bruel and Kjaer pre-amplifier type 2619.

The apparatus for carrying out the invention is compact and readily transportable. It can be located adjacent factory machinery such as a solids conveyor belt, crushers and the like. The method gives fast and reliablereadings of particle sizes, once calibrated, which is of significant benefit to industrial users. It will enable closer controls to be exerted on industrial processes such as ore crushing, to prevent unnecessary over-running of heavy crushing equipment with consequent energy wastes.

BRIEF REFERENCE TO THE DRAWINGS

DESCRIPTION OF THE PREFERRED SPECIFIC EMBODIMENT

Figure 1:
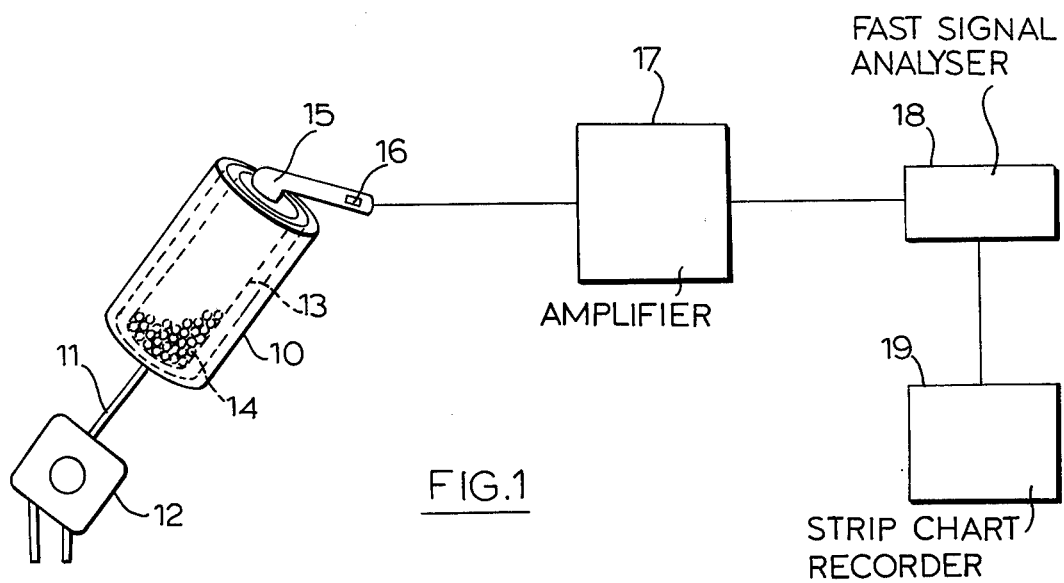
FIG. 1 is a diagrammatic illustration of an apparatus according to the invention.

With reference to FIG. 1, the apparatus comprises a drum 10 mounted at an inclined angle on a rotatable shaft 11 driven by a motor 12. The interior of the drum 10 is lined with a lining of cushioning material 13, of foam rubber. Generally spherical particles of a hard material 14 are contained as a bed within the drum 10, so that as the drum 10 is rotated about the inclined axis of shaft 11, the particles 14 are tumbled and impinge upon one another.

A microphone 15 containing a pre-amplifier 16 is mounted at the top opening of drum 10. The pre-amplifier 16 is electrically connected to an amplifier 17 which in turn is electrically connected to a fast signal analyzer 18. The fast signal analyzer 18 feeds a trip chart recorder 19. Thus, the sounds caused by impingement of the particles 14 on one another as they are tumbled by rotation of drum 10 are detected by microphone 15 and converted to electrical impulses, which are then amplified and recorded by the fast signal analyzer 18, and presented as a visual pattern by the strip chart recorder 19. The microphone is pre-set to detect and transmit sounds in the frequency range 0–200 KHz. The fast signal analyzer is pre-set to record the sound pattern produced over a period of 100 microseconds.

Figure 2:
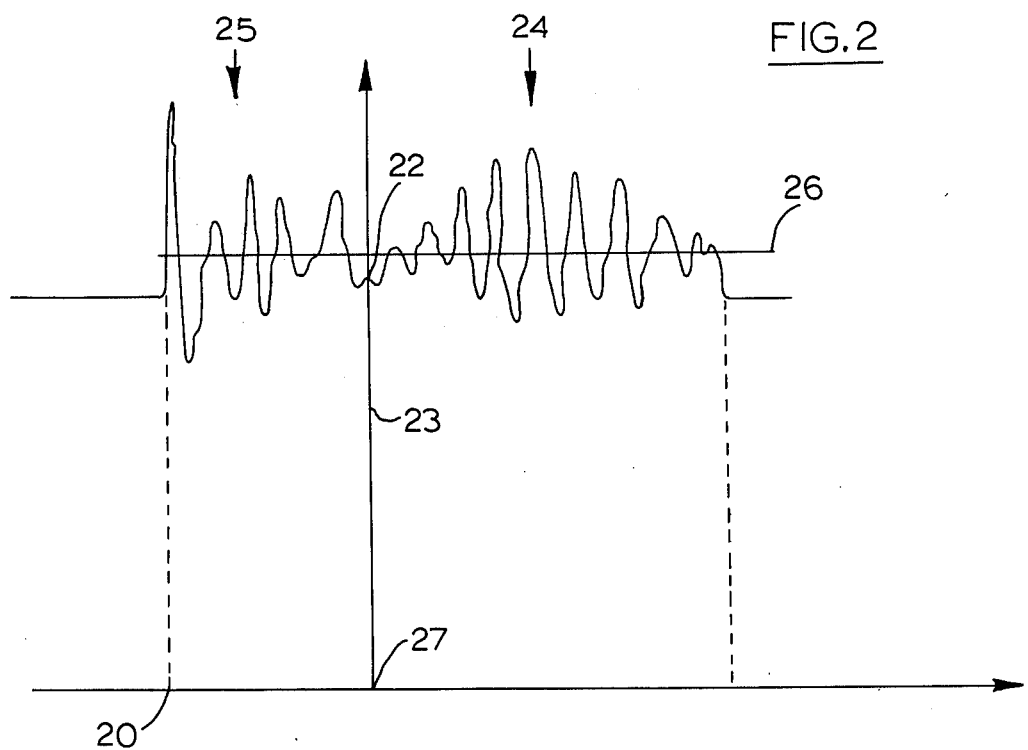
FIG. 2 is a typical sound beat pattern obtained according to the invention.

FIG. 2 shows the best pattern of sound produced by the strip chart recorder. In effect this is a graph showing the variation of the intensity or amplitude of the sound (vertical axis) with time (horizontal axis), the time interval from position 20 to position 21 on FIG. 2 being 100 microseconds. It will be seen that the pattern is of wave form. The wave of smallest amplitude, 22, represents a point of transition between the sum of the sounds of high frequency contributing to the pattern, and sum of the sounds of low frequency contributing to the pattern. In effect, this is the division between one beat and the next. Thus the vertical axis 23 is drawn to represent an approximate dividing line between the high frequency sound pattern 24 to the right, and the low frequency sound pattern 25 to the left.

A horizontal zero line 26 is drawn through the wave pattern to intersect the wave forms. It has been found that the horizontal distance (time interval) between each intersection of the wave form and the zero line 26 is substantially constant and proportional to the size of the impinging particles 14 from which the sound pattern emanates. The average intersection distance is obtained, either from the whole pattern by measuring the distance 20-21 on the chart, or by measuring only the high frequency or low frequency pattern lengths, 21-27 or 20-27, and dividing by the appropriate number of intersections.

If the pattern of FIG. 2 were recorded at a different instant of time, its superficial appearance would be different, in terms of the heights and arrangements of the various waves. However, the average intersection distance, as a time interval, is the same, and dependent upon the size of the impinging particles from which the sound emanates.

Figure 3:
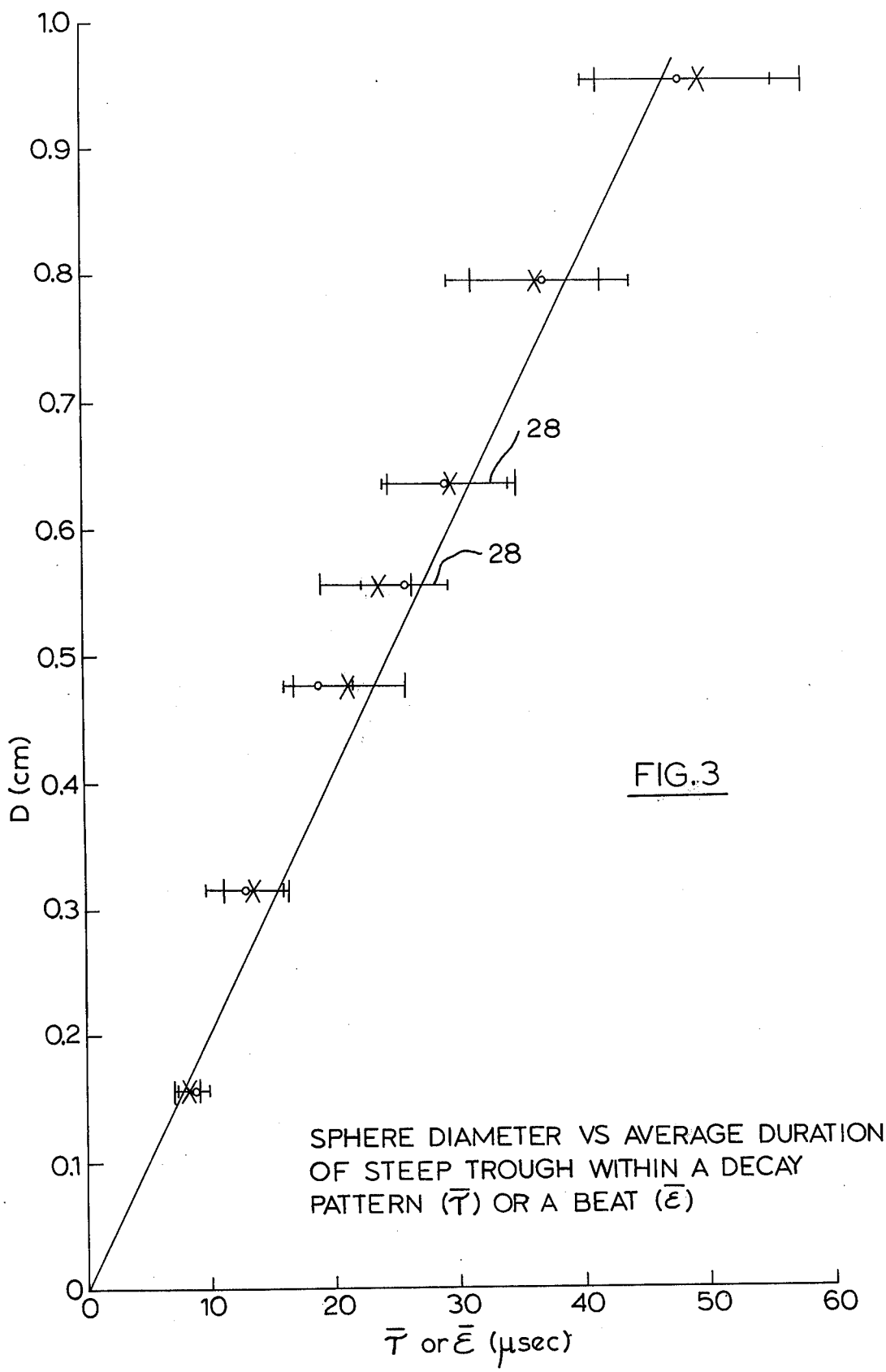
FIGS. 3 and 4 are graphs illustrating the obtaining of particle size information from a beat pattern such as that of FIG. 2.

To obtain the average particle size diameters from the average intersection distances or time intervals derived from FIG. 2, a calibration curve such as FIG. 3 is used. To obtain such a curve, measurements as described above are conducted on a series of beds of particles of known sizes. Then the average particle size diameter D (in cm.) measured in a different way, is plotted as a vertical axis against the mean time interval of waves of the beat patterns, $\bar{\tau}$ (in microseconds), and a linear curve results, as shown in FIG. 3. The curve of FIG. 3 can now be used to determine average particle diameters of any bed of particles within the applicable size range, from the readings obtained by the method of the invention.

It has further been found that the calibration curve of FIG. 3 is applicable to the whole range of hard particulate substances, the particles of which collide with substantially elastic impact. Thus the curve can be determined on a material such as steel shot, obtainable as spherical particles over a range of average particle sizes, and used to determine particle size diameter of other materials such as glass, stone, ceramics, crushed ores, rocks, aluminum, etc. As a consequence of this, the method can be used on mixtures of particles of different hard materials, i.e. non-homogeneous beds of particles.

As shown, the calibration curve of FIG. 3 is constructed by statistically averaging a selection of different values which are obtained from measuring the value of $\bar{\tau}$ for particles of known size. An identical reading of is not obtained for every measurement on the same bed of particles, since at any given instant, different resonances and harmonics of the impact produced vibrations may predominate in the beat pattern. These will lead to slight differences in the value of $\bar{\tau}$. The spread of the values is indicated by the length of the horizontal lines 28 from which the curve is constructed. The length of this line can be reduced by increasing the number of particles in the bed.

Figure 4:
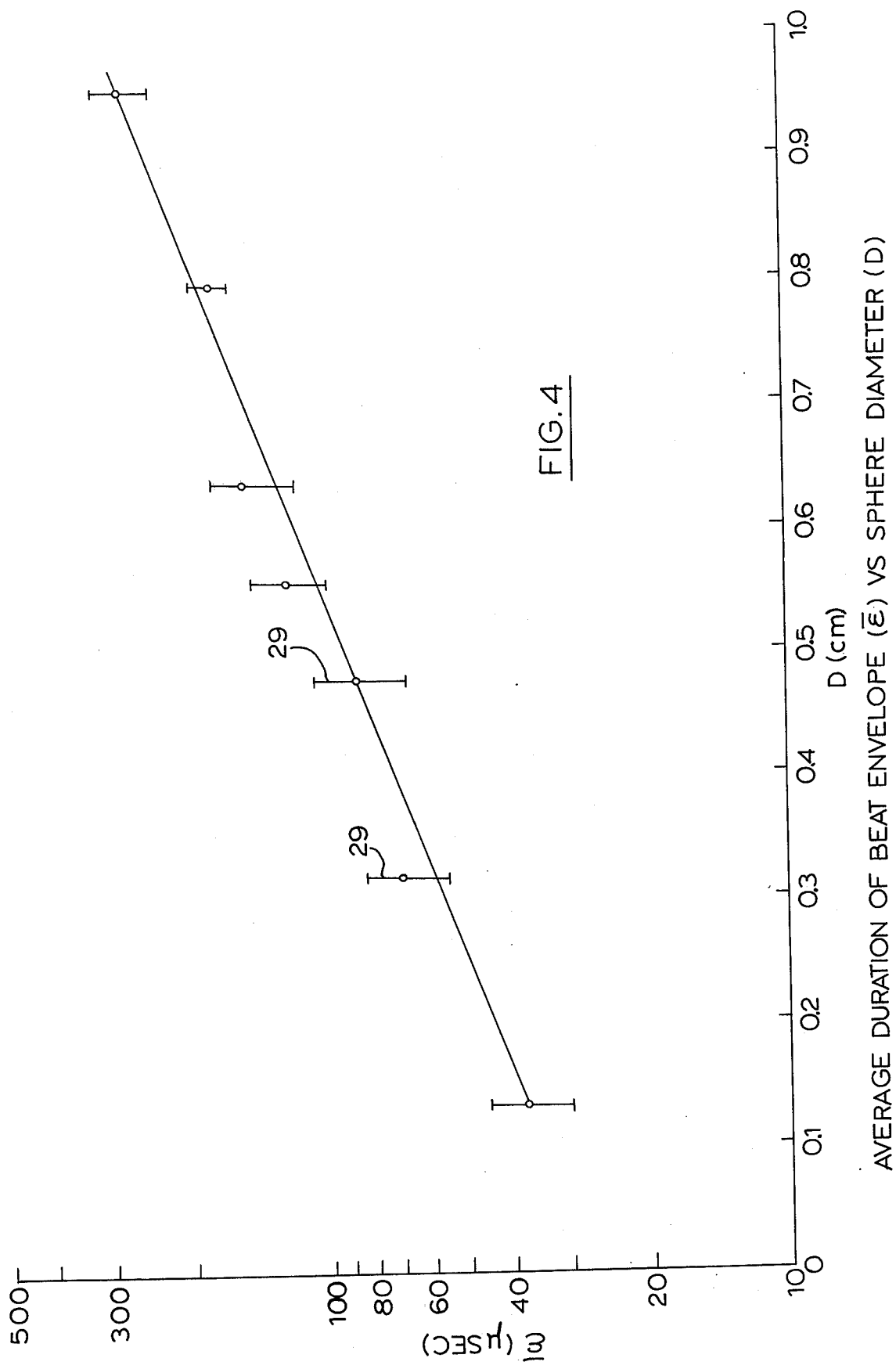

The average particle size diameter of the particles 14 can also be determined by measuring the length, in microseconds, of the high frequency portion 24 of the pattern shown in FIG. 2, i.e. the distances 21-27. It has been found that the logarithm of the distance (which is the logarithm of the duration of the beat envelope $\bar{\epsilon}$) is also related to the diameter of the particles 14 from which the sound emanates, by a linear relationship. For this purpose, a calibration curve as shown in FIG. 4 is used, where the logarithm of the average duration of the beat envelope $\bar{\epsilon}$ in microseconds is plotted as a vertical axis against the particle diameter D in centimeters. The calibration curve is constructed using known particle size material, as in the case of FIG. 3, and again points for the curve are determined by statistical averaging of values obtained and indicated by lines 29 on FIG. 4.

In the case of calibration curves of the type shown in FIG. 4, however, the precise nature of the curve differs from one material to another. Thus a separate calibration curve must be conducted for use with each different material to be tested. Thus, the nature of the material may be determined in this manner, from a knowledge of its average particle size and average duration of beat envelope, by comparison with its calibration curve.

For determining particle size distribution of the bed of particles 14, the same process is carried out but the results are differently analyzed. A time-amplitude beat pattern or curve as in FIG. 2 is determined as previously described, but over a limited range of frequencies. It is known from theoretical considerations that a particle on impingement will emit a sound having a frequency which is related to its size. The intensity of the sound emitted depends upon the number of particles. Thus, by taking a series of patterns of the type shown in FIG. 2 but over a series of different frequency ranges, and by subjecting the patterns so obtained to Fourier analysis, the intensities of the sounds emitted in that frequency range can be determined, as a percentage of the intensity of the total sound in the whole frequency range, determined by Fourier analysis of the pattern of FIG. 2. Then the series of patterns obtained at limited frequency ranges are analyzed as described with reference to the calibration curve of FIG. 3 or FIG. 4, to determine the particle sizes giving rise to that pattern. From these results, the percentage of total particle 14 having average diameters of a certain value, i.e. the particle size distribution, is readily obtained.

It will be appreciated that the above description is given by way of illustration and not limitation, the scope of the invention being defined in the appended claims.

We claim:

1. A process of determining average particle sizes and particle size distributions of a plurality of particles of a hard substance capable of substantially elastic impact together, which comprises the steps of:
impinging the particles against one another;
detecting the sound caused by such impingement;
converting the sound into corresponding electrical impulses, and recording the electrical impulses;
analyzing the beat pattern of recorded electrical impulses to determine particle size characteristics of the impinging particles generating said impulses.

2. The process of claim 1, wherein the particles are of a material selected from iron, steel, glass, aluminum, copper, hard metal, ceramic material, stone, crushed hard ore, crushed hard rock, gravel, sand, coal, sugar and salts.

3. The process of claim 1, wherein the particles are of a material having a ratio of Youngs modulus to density in the approximate range of $2\times10^7$ to $3\times10^7$ meters$^2$/second$^2$.

4. The process of claim 2, wherein the particles have diameters in the range of from 1 micron to 5 centimeters.

5. The process of claim 1, wherein high frequency sounds in the range 20–200 Kilohertz (KHz) are detected and converted to corresponding electrical impulses.

6. The process of claim 4, wherein the electrical impulses are recorded by a fast signal analyzer and the resulting pattern of time against amplitude of the sound is displayed in visual form.

7. The process of claim 1, wherein the particles have diameters in the range from about 0.1 to 10 microns, and the process includes the step of subjecting the impinging particles to ultrasound of a frequency close to that of the sound emitted by particle impingement so as to produce a sound beat as a result of the intersection of the ultrasound and the particle impingement emitted sound, and converting and analyzing said beat sound.

8. Apparatus for determining average particle sizes and particle size distribution of a hard particulate substance, which comprises in combination:
means for causing impingement of the particles against one another;
sound detecting means in proximity to the location of impingement of the particles against one another and adapted to detect the sound of said impingement and convert it to electrical impulses;
at least one amplifier electrically connected to the sound detecting means and adapted to amplify said electrical impulses;
converting means electrically connected to said at least one amplifier to convert the amplified electrical impulses to visual beat patterns or to digital information concerning said beat pattern for subsequent analysis.

9. The apparatus of claim 8, wherein said converting means comprises a flat signal analyzer adapted to isolate a sound pattern or beat of duration from about 50 to 1000 microseconds.

10. The apparatus of claim 9, wherein the fast signal analyzer is coupled to a chart recorder or a cathode ray tube and is adapted to cause visual display of the sound as a pattern of time against amplitude of the sound.

11. The apparatus of claim 9, wherein the fast signal analyzer is adapted to convert information about said sound pattern into digital form for feeding to data processing equipment.

12. The apparatus of claim 7, wherein the means for causing impingement of the particles comprises a drum adapted to rotate about an inclined exit.

13. The apparatus of claim 10, including a tunable ultrasound generator in proximity to the means for causing particle impingement, and adapted to emit ultrasound to the impinging particles of a frequency close to that of the particle impingement emitted sound.

* * * * *